United States Patent
Mizukami et al.

(10) Patent No.: US 8,384,897 B2
(45) Date of Patent: Feb. 26, 2013

(54) METHOD OF ANALYZING PARTICLE SIZE DISTRIBUTION OF PARTICLES IN METAL MATERIAL

(75) Inventors: Kazumi Mizukami, Tokyo (JP); Kenichi Murakami, Tokyo (JP); Satoshi Arai, Tokyo (JP); Nobusato Morishige, Tokyo (JP); Yuji Kubo, Tokyo (JP); Hotaka Honma, Tokyo (JP); Eiichi Nanba, Tokyo (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 318 days.

(21) Appl. No.: 12/934,031

(22) PCT Filed: Apr. 23, 2009

(86) PCT No.: PCT/JP2009/058072
§ 371 (c)(1),
(2), (4) Date: Sep. 22, 2010

(87) PCT Pub. No.: WO2009/131175
PCT Pub. Date: Oct. 29, 2009

(65) Prior Publication Data
US 2011/0019187 A1 Jan. 27, 2011

(30) Foreign Application Priority Data
Apr. 25, 2008 (JP) .................................. 2008-114801

(51) Int. Cl.
*G01N 15/02* (2006.01)
(52) U.S. Cl. ...................................................... 356/335
(58) Field of Classification Search .................. 356/335, 356/336
See application file for complete search history.

(56) References Cited

U.S. PATENT DOCUMENTS

| 4,724,134 A * | 2/1988 | Sood ........................ 423/592.1 |
| 5,985,674 A | 11/1999 | Umezawa et al. |
| 6,774,994 B1 | 8/2004 | Wyatt et al. |

(Continued)

FOREIGN PATENT DOCUMENTS

| EP | 1 884 762 A2 | 2/2008 |
| JP | 60-216253 A | 10/1985 |

(Continued)

OTHER PUBLICATIONS

Cui-fen Lu et al.; The methods of laser size analysis of stabilize oxide inclusion in steel; The 13th A & T Conf. of Central Iron & Steel Research Institute; Oct. 31, 2006; pp. 509-514 (Abstract appears on p. 514).

(Continued)

*Primary Examiner* — Roy M Punnoose
(74) *Attorney, Agent, or Firm* — Birch, Stewart, Kolasch & Birch, LLP

(57) ABSTRACT

A method according to the present invention has: isolating, by extraction, particles contained in a metal material to be analyzed in a solution using a particle isolator; dispersing the particles isolated by extraction into a solvent to prepare a dispersion, and fractionating the dispersion into a plurality of particle dispersions based on particle sizes, using a field flow fractionator; and irradiating laser light on each of the particle dispersions separated based on predetermined particle sizes, to thereby measure absolute values of the particle size based on angular dependence of reflection intensity, and also to thereby measure the number density based on magnitude of reflection intensity.

9 Claims, 5 Drawing Sheets

U.S. PATENT DOCUMENTS

| | | | |
|---|---|---|---|
| 7,294,513 B2 * | 11/2007 | Wyatt | 436/45 |
| 2007/0166828 A1 | 7/2007 | Strothers et al. | |
| 2008/0285032 A1 | 11/2008 | Ohkubo | |
| 2010/0206736 A1 | 8/2010 | Ishida et al. | |

FOREIGN PATENT DOCUMENTS

| | | |
|---|---|---|
| JP | 5-346387 A | 12/1993 |
| JP | 10-26618 A | 1/1998 |
| JP | 10-300659 A | 11/1998 |
| JP | 2004-317203 A | 11/2004 |
| JP | 2005-62166 A | 3/2005 |
| JP | 2007-127454 A | 5/2007 |
| JP | 2008-724 A | 1/2008 |
| JP | 2008-39539 A | 2/2008 |
| JP | 2009-19956 A | 1/2009 |
| WO | WO 02/29400 A2 | 4/2002 |
| WO | 2006/082431 A1 | 8/2006 |
| WO | 2007/081610 A1 | 7/2007 |
| WO | 2009/005111 A1 | 1/2009 |

OTHER PUBLICATIONS

Database WPI, Thomson Scientific, Abstract, AN 1985-308171, XP-002639017, Week 198549 (1 page).

Extended European Search Report dated Jun. 8, 2011, for European Application No. 09733952.7.

Camp-Isij, "Development of analysis method for particle size distribution and chemical composition of oxides in steel by optical emission spectroscopy", vol. 14, pp. 813-816, 2001.

Chino et al., "The Measurement of Particle Size Distribution of Al2O3 Inclusion in Ultra Low Oxygen Steel", Journal of the Iron & Steel Institute of Japan, 1991, vol. 77, No. 12, pp. 95-102.

International Search Report dated Aug. 4, 2009 for PCT/JP2009/058072.

JIS G 0555: 2003, "Microscopic testing method for the non-metallic inclusions in steel", Published by Japanese Standards Association, ICS 77.040.99, pp. 1-52, Revised Jun. 20, 2003.

Kurosawa et al., "Observation of Precipitates and Metallographic Grain Orientation in Steel by a Non-aqueous Electrolyte-Potentiostatic Etching Method", Journal of Japan Institute of Metals, vol. 43, pp. 1068-1077, 1979.

Reinholdsson et al., "A Metallurgical Tool for Rapid Determination of Micro Inculsion Characteristics in Bearing Steel Production" ISIJ International, vol. 37, No. 6, 1997, pp. 637-639.

Wyatt et al., "High-Precision Measuremenf of Submicrometer Particle Size Distributions", Langmuir, Vo. 13, No. 15, 1997, pp. 3913-3914.

\* cited by examiner

METHOD OF ANALYZING PARTICLE SIZE DISTRIBUTION OF PARTICLES IN METAL MATERIAL

TECHNICAL FIELD

The present invention relates to a method of analyzing particle size distribution of particles (precipitations and non-metallic inclusions) in metal material adopting field flow fractionation (FFF).

BACKGROUND ART

In recent years, there has been a growing demand for higher quality of metal materials. Relatively large inclusion possibly generated in the process of deoxidation of steel or the like is causative of considerable degradation in steel quality. For example, aluminum-series oxides may induce various non-conformities such as surface defect on a thin automotive steel sheet, crack in a process of manufacturing a beverage can, breaking of wire products in a process of drawing, and so forth. Numerous efforts have, therefore, been made aiming at reducing the amount and size of such inclusions.

On the other hand, also numerous efforts have been made in order to intentionally increase or decrease the amount and size of fine inclusions, so as to further improve quality of steel. For example, efforts have been made on allowing a significant amount of fine precipitates to precipitate in steel, or downsizing grain size of steel, during various processes of hot rolling, cold rolling, and heat treatment such as continuous annealing, stress relief annealing, welding and so forth, to thereby improve strength and toughness of welded portion. Efforts have been made still also on reducing the amount of fine precipitates, and increasing coarse grains, to thereby improve the iron loss.

Accordingly, for the purpose of highly-reproducible mass production of high-quality steel on the industrial basis, conventional analytical values of component alone may be insufficient to fully understand the amount and size of particles contained in steel, so that it is important to develop a method of analyzing particle size distribution of particles in steel, capable of validating the amount and size of the particles in a correct and highly reproducible manner.

Conventionally known methods of inspecting particles in steel include microscopic inspection methods such as ASTM method, JIS method, and a MICHELIN method developed by MICHELIN. For example, a microscopic inspection method specified by Non-Patent Document 1 is such as polishing a metal sample, and observing the metal sample under a microscope at least in 60 or more field of views at a 400× magnification in principle, so as to judge the degree of cleanliness of steel based on the ratio of area occupied by particles such as inclusion. All of these conventional methods rely upon visual inspection under an optical microscope, and therefore suffer from slow speed of inspection. Another problem is that the methods suffer from large error, and are therefore difficult to ensure highly accurate measurement, because there is no obvious rule for discriminating the inclusions from misconceptional factors such as dust, polishing defect, rust and so forth.

Patent Document 1 describes a method aimed at making up for low number density in this sort of microscopic observation. In this conventional method, steel is electrolyzed first, and the extracted residue is then dropped onto a support film and allowed to dry, to thereby produce a sample having an extremely large number of residue particles. The sample is then subjected to optical microscopic analysis, scanning electron microscopic (SEM) analysis, transmission electron microscopic (TEM) analysis and so forth. Patent Document 1 also describes that an effect of this sort of method is such that a highly representative particle size distribution data contributed by a large number of particles may be obtained.

However, in this method, the sample contains large particles and small particles in a mixed manner. Accordingly, in order to measure a distribution over the entire sizes from the individual photos in the microscopic analysis, a large number of times of photographing and image processing, and even a manual counting by an operator, may be necessary. It may, therefore, be impossible to improve the speed of inspection, and may be difficult to obtain good reproducibility due to a large tendency of causing individual difference.

Another method of evaluation different from the microscopic inspection is described in Patent Document 2 and Non-Patent Document 2. According to the method of evaluation, a metal sample is subjected to optical emission spectrometry under spark discharge induced by approximately 2,000 pulses, in which particle size of oxide is determined based on discharge data exclusive of a preliminary discharge data corresponded to initial several hundred pulses. In this method of evaluation, a very intense optical emission (abnormal emission) ascribable to constitutive element of the oxide is assumed as being derived from a single oxide particle.

Still another method of determining the size and frequency of alumina inclusion is described in Non-Patent Document 3. In this method, a metal sample is subjected to optical emission spectrometry under spark discharge, and the size and frequency of alumina inclusion are determined based on intensity of optical emission spectrometric data, while assuming that only pulse data exceeding a predetermined threshold value is ascribable to the inclusion and so forth.

These methods, relying upon optical data processing of optical information called optical emission intensity, are less causative of individual difference, and therefore advantageously enable compositional analyses making use of simultaneous optical emission by multiple elements.

However, these methods are not considered to be highly accurate, since the hypotheses described in Patent Document 2 and Non-Patent Document 2 are incorrect. More specifically, so far as actual traces of discharge of several millimeters in diameter are observed, it may be natural to suppose that "a single time of pulse emission is ascribable to a plurality of particles of inclusion (oxide)", so that the hypothesis described in the above are not correct.

In addition, since the particles such as inclusion contributive to the optical emission in these methods of optical emission spectrometry are larger than several micrometers in principle, so that pulse intensity of the particles cannot be compared with that of the solid-solubilized components in the matrix, unless the particles have such large sizes. In other words, the optical emission spectrometry is not adoptable to particles having sizes smaller than several micrometers, and this makes the analyses incorrect.

As has been described in the above, it is very important to quantitatively analyze the size, frequency and composition of particles in metal in a rapid and correct manner, in view of quality control of metal materials. This is, however, not attainable by the prior arts.

CITATION LIST

Patent Literature

Patent Document 1: Japanese Laid-Open Patent Publication No. 2004-317203
Patent Document 2: Japanese Laid-Open Patent Publication No. H10-300659
Patent Document 3: Japanese Laid-Open Patent Publication No. 2005-62166

Non-Patent Literature

Non-Patent Document 1: JIS-G-0555
Non-Patent Document 2: CAMP-ISIJ, Vol. 14, 2001, p. 813
Non-Patent Document 3: ISIJ International, Vol. 37, 1997, No. 6, p. 637
Non-Patent Document 4: Journal of Japan Institute of Metals, Vol. 43, p. 1068 (published on Nov. 20, 1979)
Non-Patent Document 5: J. P. Wyatt, D. N. Villalpando, Langmuir, 13(1997), p. 3913

SUMMARY OF THE INVENTION

Technical Problem

It is therefore an object of the present invention to provide a method of analyzing particle size distribution of particles in metal material, capable of quantitatively analyzing the size and number density of particles contained in a metal material in a rapid and correct manner, and preferably capable of quantitatively analyzing also composition and crystal structure of the particles in a rapid and correct manner.

Solution to Problem

The present invention is accomplished aiming at solving the above-described problems, and may be summarized as follows:

(1) A method of analyzing particle size distribution of particles in metal, comprising:
  isolating, by extraction, particles contained in a metal material to be analyzed in a solution using a particle isolator;
  dispersing the particles isolated by extraction into a solvent to prepare a dispersion, and fractionating the dispersion into a plurality of particle dispersions based on particle sizes, using a field flow fractionator; and
  irradiating laser light on each of the particle dispersions separated based on predetermined particle sizes, to thereby measure absolute values of the particle size based on angular dependence of reflection intensity, and also to thereby measure the number density based on magnitude of reflection intensity.

(2) The method of analyzing particle size distribution of particles in metal according to (1), wherein the particles have sizes of 20 μm or smaller.

(3) The method of analyzing particle size distribution of particles in metal according to (1) or (2), wherein the solvent is an organic solvent.

(4) The method of analyzing particle size distribution of particles in metal according to any one of (1) to (3), wherein a solvent containing a surfactant is used as the solvent.

(5) The method of analyzing particle size distribution of particles in metal according to any one of (1) to (4), wherein the particles are isolated by extraction based on an electrolytic method using a non-aqueous solvent system.

(6) The method of analyzing particle size distribution of particles in metal according to (5), wherein the electrolytic method using a non-aqueous solvent system is a potentiostatic electrolytic method using a non-aqueous solvent system.

(7) The method of analyzing particle size distribution of particles in metal according to (5) or (6), wherein isolation by extraction of the particles based on the electrolytic method using a non-aqueous solvent system is carried out with using a non-aqueous solvent base electrolytic solution containing a surfactant.

(8) The method of analyzing particle size distribution of particles in metal according to any one of (1) to (7), further comprising, after measuring the number density, analyzing composition of the particles.

(9) The method of analyzing particle size distribution of particles in metal according to any one of (1) to (8), further comprising, after measuring the number density, analyzing crystal structure of the particles.

Advantageous Effects of Invention

According to the present invention, size and number density of particles contained in metal material may be quantified in a rapid and highly reproducible manner. As a consequence, the particle size distribution may be measured with high accuracy.

DESCRIPTION OF EMBODIMENTS

Figure 1:
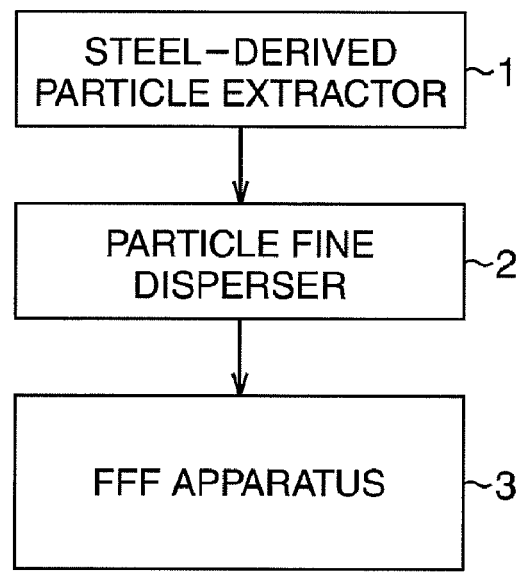
FIG. 1 is a flow chart illustrating a basic flow of a method of analyzing particle size distribution of particles in a metal material, according to an embodiment of the present invention.

Preferred embodiments of the present invention will be detailed below, referring to the attached drawings. Note that, in this patent specification and attached drawings, all constituents having substantially identical function and configuration will be given the same reference numbers or numerals, so as to avoid repetitive explanation.

An essential point of the present invention is to enable rapid and correct quantification of the size and number density of particles contained in a metal material to be measured. It is, therefore, important to overcome the problems related to erroneous and time-consuming nature specific to the conventional sensory inspection, and also to enable highly-reproducible measurement of the size and number density, for the purpose of providing a method of clearly understanding the number density of particles having a size of not larger than several micrometers, which have not been detectable by any method of estimation based on optical emission spectrometry.

Considering now an operation of counting the number of particles on a microphotograph, having very large particles and very small particles of a plurality of sizes imaged in a mixed manner in a single picture, the operator has to measure the size of the individual particles one-by-one, and has to finally count up the number of particles. Taking now also representativeness of sample into consideration, a probability that a very large particle is detectable in a single photo is low, so that it may therefore be necessary to take pictures in a large number of fields of view. On the other hand, as for very small particles, even a single photo may contain several thousands or more particles, so that it may be necessary to count up the number of particles in the same area with an unnecessarily large load of operation. Moreover, since the size may occasionally vary over a wide range from the order of nanometers up to the order of several tens of micrometers, so that it may be necessary to take photos while varying magnification. The present inventors extensively discussed whatever factor could most adversely affect the efficiency of working, and finally reach an inevitable conclusion that imaging of the particles of a plurality of sizes and counting of the number thereof in a single photo per se is unreasonable.

More specifically, statistically representative data of large particles may not be collected, unless wider fields of view are observed at low magnifications. On the other hand, size and quantity of small particles may not correctly be judged unless the magnification is elevated, but this makes it difficult to obtain collect values while being shadowed by the large particles, for example. In order to solve the contradiction, the present inventors finally concluded that it may be important, for correct and rapid evaluation, to preliminarily fractionate the particles by sizes, and then to measure and evaluate the particles by methods suitable for the respective sizes.

The present inventors then examined a method of imaging the particles after screening them by sizes. However, even the smallest mesh size of the currently-available metal screen is 20 μm or around, so that it is difficult to fractionate further smaller particles by size. The present inventors then made our efforts specialized to find a method of fractionating, by size, 20 μm or smaller particles to be measured.

Any atoms or molecules having different mass numbers may directly be ionized, and then be subjected to mass analysis, or to isolation and extraction by ion chromatography, so as to determine the size and quantity thereof. In contrast, the particles in steel are far larger than those in biological samples, and are difficult to be ionized by soft processes. Also ionization by solubilization is not adoptable, since information on size may be erased by solubilization. In general, ionized species are not explicitly charged in solution to produce positive ions or negative ions, and are therefore even impossible to fractionate them by ion chromatography or the like.

The present inventors also investigated into size fractionation by GPC (gel permeation chromatography), only to find it inappropriate for the purpose of precise fractionation of a trace amount of ions. Measurable molecular weight by the method ranges widely from several hundreds to several tens of millions, but even the upper limit of molecular weight in the order of several tens of millions is still too low to fractionate the actual particles in metal materials having the size ranging from several nanometers to several tens of micrometers. In addition, also a large amount of ample is necessary.

The present inventors actually investigated through a plurality of means for separation and analysis as described in the above, and at last successfully reached the field flow fractionation (FFF) process which is worth to be put into practical use as a method of fractionating the particles by size.

In the present invention, the particles are preliminarily fractionated by size, in order to quantify the number density of the particles in a metal material in a rapid and highly reproducible manner.

FIG. 1 illustrates a basic flow of a method of analyzing particle size distribution of particles in a metal material, according to an embodiment of the present invention. A particle fractionator used in this embodiment has a steel-derived particle extractor 1, particle fine disperser 2, and a FFF apparatus 3, as the major constituents. In the method of analyzing particle size distribution according to the present embodiment, first, the particles contained in a metal material are stably extracted using the steel-derived particle extractor 1. The particles derived from the metal material are then finely dispersed in a solution using the particle fine disperser 2 without causing agglomeration. The particles derived from the metal material and dispersed into the solution are then placed in the FFF apparatus 3, and then subjected to fractionation by size, measurement of size, and measurement of number density. Exemplary operations of the FFF apparatus 3 will be explained below.

For example, according to the fractionation by size, based on the FFF process described in Non-Patent Document 5, the particles in the solution are poured in the FFF apparatus, fractionated by size by focusing, and allowed to discharge in the increasing order of size, so as to obtain smaller particles earlier and larger particles later. The obtained fractions of the solution are irradiated by laser light, to thereby determine absolute values of the particle size based on angular dependence of reflection intensity, and also to thereby determine the number density based on magnitude of reflection intensity.

Based on the knowledge described in the above, the method of analyzing particles in metal material according to this embodiment will be detailed.

Figure 2:
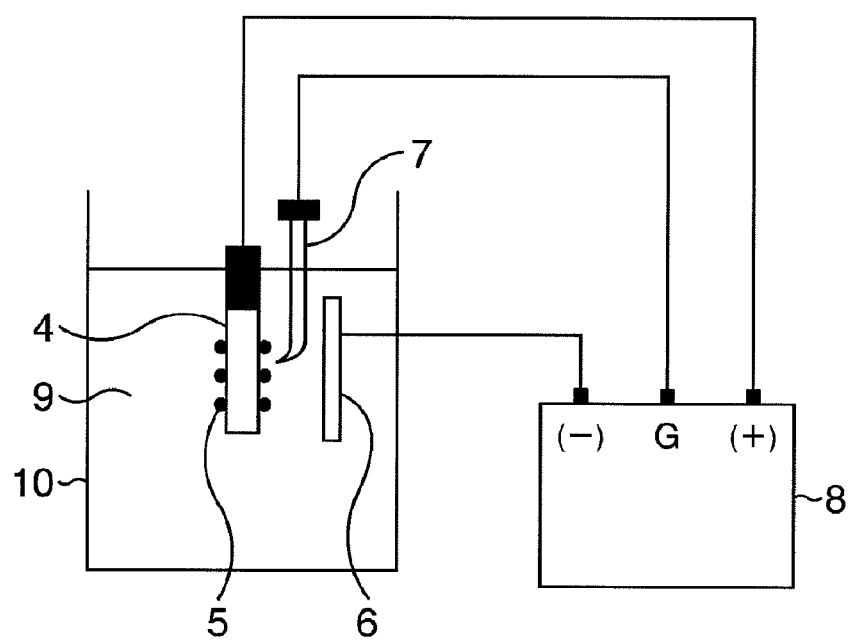
FIG. 2 is a drawing illustrating an example of a steel-derived particle extractor 1.

The steel-derived particle extractor 1 is an apparatus used for stably extracting particles from metal. FIG. 2 is a drawing illustrating an example configuration of the steel-derived particle extractor 1. The method of extracting the particles from a metal sample according to this embodiment may be exemplified by acid decomposition method by which an iron matrix of a steel sample is dissolved in an acid solution; halogen dissolution method by which an iron matrix of a steel sample is dissolved in an iodine-methanol mixed solution or in an bromine-methanol mixed solution; a static current electrolytic method using a non-aqueous solvent system; or a static potential electrolytic method using a non-aqueous solvent system (SPEED: selective potentiostatic etching by electrolytic dissolution). Among these, the SPEED is preferable, since the particles are less likely to cause compositional and dimensional changes even after being dispersed into a solvent, and even unstable particles may stably be extracted. Details of the SPEED are described, for example, in Non-Patent Document 4. This embodiment will be explained below, while exemplifying a method of evaluating particles in a steel material, based on the SPEED process. The method of extraction in the present invention is, however, not limited to the SPEED, and the metal material is not limited to the steel material.

First of all, a metal sample 4 is cut, for example, into a 20 mm×40 mm×2 mm piece, and subjected to chemical polishing, mechanical polishing or the like, so as to remove an oxide film and the like such as scale or the like, to thereby expose the metal layer. On the contrary, the oxide film and the like is left unremoved, for the case where the particles contained therein is an object to be analyzed.

Next, the metal sample 4 is subjected to electrolysis by the SPEED. More specifically, an electrolytic solution 9 is filled in an electrolytic bath 10, the metal sample 4 is immersed therein, and a reference electrode 7 is brought into contact with the metal sample 4. A platinum electrode 6 and the metal sample 4 are connected to an electrolytic unit 8. In general, in this sort of electrolytic method, particles in steel, such as precipitates, will have an electrolytic potential higher than that of a metal portion composing the matrix of the metal sample 4. Accordingly, only the matrix may selectively be dissolved, by setting the voltage of the electrolytic unit 8 in a range causative of dissolution of the matrix of the metal sample 4, but not causative of dissolution of the particles such as precipitates. Electrolytically-extracted particles 5 appear in the surficial portion of the metal sample 4, and disperse into the electrolytic solution 9.

The electrolytically-extracted particles 5 dispersed into the electrolytic solution 9 are then separated and collected by filtration, and then placed in a fresh solvent together with the metal sample 4. The system is then irradiated by ultrasonic wave or the like, to thereby desorb the electrolytically-extracted particles 5, having been adhered onto the surficial portion of the metal sample 4, from the metal sample 4. As a consequence, a particle extraction solution, which contains electrolytically-extracted particles 5 extracted from the metal sample 4, may be obtained. Whichever solvent of aqueous base or organic solvent base may be adoptable, where organic solvent is preferable, in view of keeping the electrolytically-extracted particles 5, such as inclusion, in a stable manner without causing dissolution. Among organic solvents, alcoholic solvents, such as methanol and ethanol, are readily available and highly stable.

The conventional potentiostatic electrolytic method adopts, for example, a 10% by mass acetylacetone (referred to as "AA", hereinafter)/1% by mass tetramethylammonium chloride (referred to as "TMAC", hereinafter)/methanol solution, or a 10% by mass maleic anhydride/2% by mass TMAC-methanol solution, as the electrolytic solution. There is an alternative case of using an electrolytic solution obtained by dissolving a chelating agent, such as methyl salicylate, capable of forming a chelate complex with a metal ion, and an electrolyte such as tetramethylammonium chloride (TMAC) allowing electric current to flow, into a non-aqueous solvent represented by methanol. These sorts of electrolytic solution are widely used by virtue of their desirable work efficiency and stability in extraction.

The present inventors newly found out that electrolytically-extracted particles 5, such as inclusions, may further stably be captured, by using a solution prepared by adding a dispersant mainly composed of a surfactant described later to these sorts of electrolytic solution, as the electrolytic solution 9. By virtue of addition of the surfactant, the electrolytically-extracted particles 5 immediately after being desorbed from the metal matrix and released into the electrolytic solution 9 may be stably surrounded by the surfactant.

By preliminarily adding the dispersant also to the electrolytic solution 9, which is a non-aqueous electrolytic solution, the electrolytically-extracted particles 5 released from the metal material 9, such as steel or the like, may stably be surrounded by the dispersant before being brought into contact with the air, and thereby the effect of extraction is improved. The addition may make another effect of readily and rapidly obtaining monodisperse particles, also when the electrolytically-extracted particles 5, such as inclusions, are re-dispersed later into a solvent. For this reason, it may be important to carry out all processes, from the extraction of the electrolytically-extracted particles 5 to the fractionation into the fractions of the individual particle sizes, in the liquid so as to prevent the electrolytically-extracted particles 5 from being brought into contact with the air.

By virtue of this operation, the electrolytically-extracted particles 5 may now be extracted in a stable and efficient manner, even if they are very labile, for example, to chemicals and/or water. The concentration of the surfactant to be added is preferably 0.0001% by mass to 10% by mass. The concentration lower than 0.0001% by mass is too low to sufficiently express the operation. On the other hand, an excessively high concentration makes the solution foamier, and is undesirable in view of work efficiency.

Figure 3:
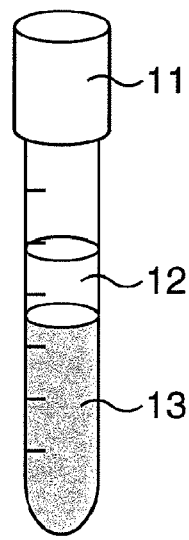
FIG. 3 is a drawing illustrating an example of a method of preparing a solution used for a particle fine disperser 2.

FIG. 3 is a drawing illustrating an example of a method of preparing the solution adopted for the particle fine disperser 2. An extracted particle-containing liquid 13 prepared by ultrasonic irradiation as described in the above, in other words, a liquid containing the electrolytically-extracted particles 5 extracted from the metal sample 4 using the steel-derived particle extractor 1, is placed in a liquid vessel 11, and is added with a dispersant 12, for the purpose of further finely dispersing the electrolytically-extracted particles 5. A surfactant, for example, may be adoptable as the dispersant. Alternatively, the electrolytically-extracted particles 5 may be dispersed also after being elevated in the surface potential thereof, typically by adjusting the zeta potential through pH control. It should be noted that the method of using a surfactant as the dispersant may be more effective.

The surfactant has, in the molecule thereof, a portion having a high affinity to water (hydrophilic group), and a portion having a high affinity to oil (oleophilic group, or hydrophobic group). In a general procedure of dispersing particles into a solution, a surfactant are allowed to adhere onto the surface of the particles, to thereby make the periphery of the particles charged positive or negative. As a consequence, repulsive force generates between the adjacent particles having the same polarity, and thereby the individual particles may be dispersed. The surfactant may roughly be classified into those having ionic (cationic/anionic) hydrophilic portion and those having nonionic hydrophilic portion.

The anionic surfactant dissociates in water to produce an anion, the hydrophilic group of which typically has a structure of carboxylic acid, sulfonic acid, phosphoric acid or the like. The carboxylic acid-type surfactant may be represented by fatty acid salt, which is a major constituent of soap, and cholic acid; and the sulfonic acid-type surfactant may be represented by sodium linear alkylbenzene sulfonate, and sodium lauryl sulfate.

The cationic surfactant dissociates in water to produce a cation, the hydrophilic group of which typically contains tetraalkyl ammonium. Representative species include alkyl-trimethyl ammonium salt, dialkyl-dimethyl ammonium salt, and alkyl-benzyl-dimethyl ammonium salt.

After extensive investigations into efficacy of these various species of surfactant, both of the anionic surfactant and the cationic surfactant were found to be effective as the dispersant 12. Among others, sodium salt of mono(long-chain alkyl) ester represented by sodium lauryl (or dodecyl) sulfate ($C_{12}H_{25}NaO_4S$: SDS) is preferable, by virtue of its relatively good availability and popular uses in the field of biochemistry. The substance is contained also in daily goods such as toothpaste, shampoo and so forth, proven to be safe to human body and is inexpensive.

Besides them, amphiphilic surfactant having, in the molecule thereof, both of an anionic portion and a cationic portion, and nonionic surfactant having a non-ionizable hydrophilic portion, may be adoptable as the dispersant 12.

Approximately 1 ml to 20 ml, preferably 10 ml or around, of the extracted particle-containing liquid 13 containing the electrolytically-extracted particles 5, such as inclusions extracted from the metal material 4 such as steel, is sampled in a liquid vessel 11, such as test tube, added with 2 ml of the dispersant solution 12 having an SDS concentration of 0.0001% by mass to 10% by mass, preferably 0.05% by mass or lower, and the particles are allowed to disperse under ultrasonic irradiation for 1 min. to 10 min., preferably for 3 min. or around. The extracted particle-containing liquid 13 may be very dense or very dilute, both of which may cause an excessive load to a measuring instrument. It may, therefore, be preferable to adjust the number density in an optimum range. For this reason, the volume may preferably be adjusted at least to 1 ml, and 20 ml or around at most. The concentration of SDS may be adjustable to any range, so far as SDS may keep dispersibility exerted on the electrolytically-extracted particles 5, where the lowest possible concentration is preferable. Note that the concentration lower than 0.0001% by mass may result in only a small effect of dispersion, whereas too high concentration may increase the cost, and may also undesirably make the solution more foamy.

Length of time of the ultrasonic irradiation may vary depending on the output power and the volume of liquid, where the mixed liquid of the extracted particle-containing liquid 13 and the dispersant 12 may be overheated and denatured, if allowed to stand for longer than 10 minutes. On the other hand, the length of time shorter than one minute may result in only an insufficient degree of dispersion.

A solution having the electrolytically-extracted particles 5 dispersed therein may thus be obtained, wherein the size of the electrolytically-extracted particles 5 contained therein widely ranges, so that some method of measurement may suffer from a problem that coarse fraction of the electrolytically-extracted particles 5 may obstruct a small hole inside the FFF apparatus 3, or may clog a filter. It may therefore be preferable to preliminarily eliminate the coarse fraction of the electrolytically-extracted particles 5. For example, preliminary filtration through a several-micrometer-mesh filter may be preferable. Alternatively, coarse particles of 1 µm or larger may be sedimented in a centrifugal machine over several minutes, and the supernatant of the resultant liquid may be charged to the FFF apparatus 3.

Principle of the size fractionation by the FFF process will be explained below, referring to FIG. 4. A fractionation solution containing a surfactant is used as an eluant for the FFF apparatus 3. In the initial stage, a liquid flow called cross-flow 14 is generated in the direction from the top to the bottom of the fractionation cell 16, at the same time the liquid is allowed to flow also from the left and right, and a sample liquid 15 containing the particles is placed in between. Large particles 20 having a larger size adhere to a separation membrane 21 on the lower side while being pressed by the cross-flow 14, whereas relatively larger middle-sized particles 19 and small particles 18 floats in the fractionation cell 16 in a size-dependent manner, without being tightly pressed against the separation membrane 21 on the lower side of the fractionation cell 16, by virtue of the Brownian motion capable of overwhelming the cross-flow 14. The state is called "focusing". By achieving the state, the particles are re-located in the fractionation cell 16 in a size-dependent manner. Thereafter, the flow having been applied so as to press the fractionation cell 16 from the left and right is changed to produce channel flow 17, and thereby the particles having been arranged in the fractionation cell 16 are pushed out, for example, in the direction from the left to right in FIG. 4.

In this process, by gradually reducing the pressure of the cross-flow 14, having been applied so as to press the separation membrane 21 downward, towards zero, the particles having been pressed closer to the separation membrane 21 are sequentially discharged in a manner such that the smaller particles come earlier, and larger particles come later.

While the description herein dealt with the case where the size fractionation is accomplished by a combination of the pressurizing force of the cross-flow liquid and the Brownian motion, the particles may more precisely be fractionated based on other types of principle of FFF, making use of gravity, electric field, magnetic field, temperature gradient and so forth applied thereto.

The liquids fractionated in a size-dependent manner are then directly introduced into a laser irradiation detector placed in the FFF apparatus 3, and intensity of scattered laser light is measured using photodetectors disposed at a plurality of angular positions. The smaller particles, having a very small angular dependence, give omnidirectional scattering. On the other hand, the coarser particles give more intense front scattering, so that the size of the electrolytically-extracted particles 5 may unconditionally be determined, by finding a slope of the angular dependence.

For more details, typically by the Zimm plot method, the size of the electrolytically-extracted particles 5 may be calculated based on the angular dependence. The Zimm plot method will be briefed below. Relations among angle of scattering, concentration, molecular weight and second virial coefficient representing the state of dispersion of the particles may be given by the Rayleigh's equation below:

$$K \times C/Ra = (1/M + 2A_2 \times C) P(\theta)$$

K: optical constant;
C: concentration;
Ra: Rayleigh ratio of solvent;
M: molecular weight;
$A_2$: second virial coefficient; and
$P(\theta)$: angle-dependent function.

As obvious from the above, the equation contains variables relevant to concentration and angle, and may be given as a proportional equation if the concentration is fixed. When changes in the quantity of scattered light is measured under varied concentration and varied angle of scattering, a value obtained at an angle of 0°, under zero concentration represents molecular weight. A plot of these values is called the Zimm-Berry plot.

In the method of particle size measurement according to this embodiment, quantities of scattered light obtained under constant concentrations are extrapolated to angle $\theta = 0$ to obtain a plot, from which an inverse of molecular weight is known, where the slope of the plot represents the mean square inertia diameter. As a consequence, by finding the slope of the angle dependence, the size of the electrolytically-extracted particles 5, or the particles in the metal material, may unconditionally be determined.

Since the observed intensity of scattered light is known to increase in proportion to the number density of the electrolytically-extracted particles 5 contained therein, so that the number density of the particles in the liquid may readily be found, by preliminarily preparing a relational equation between the intensity of scattered light and the number density.

The lower limit value of the particle size adoptable to the FFF apparatus 3 is 1 nm, for example. The particles having smaller sizes are difficult to be adopted, because of close proximity with the separation performance of the regenerated cellulose film used for separating the electrolytically-extracted particles 5 from the liquid, and increased possibility of permeation through the regenerated cellulose film.

In addition, according to the method of measuring particle size of this embodiment, each liquid fractionated by size may further be subjected to compositional analysis of the electrolytically-extracted particles 5, which are the particles in the metal material 4. Any arbitrary method selected from various mass analyses, spectrometric analyses, chemical analyses and so forth, may be adoptable as the methods of compositional analysis. By carrying out compositional analysis of the liquid after being measured with respect to the particle size, it is now possible to clarify that from which component of the metal material 4 are the particles, having been measured with respect to the particle size, derived from.

EXAMPLE

Examples of the present invention will be explained below. Note that the present invention is not limited to the conditions adopted in the Examples.

According to the flow illustrated in FIG. 1, the particles in a steel material were extracted and dispersed into a liquid, and then measured with respect to the size and number density, using the FFF apparatus, by the method of particle analysis according to the embodiment.

A high-Si steel sample (Si: 3% by mass, Mn: 0.1% by mass, S: 0.03% by mass, Al: 0.03% by mass, N: 0.01% by mass) was processed into a 20 mm×40 mm×0.3 mm size, and subjected to chemical polishing so as to remove an oxide film and the like such as scale or the like in the surficial portion, to thereby expose the metal layer. In this process, the high-Si steel sample was sampled from each of steel materials manufactured under normal temperature condition (1000° C.), and under higher temperature condition (1100° C.) higher by approximately 100° C. than the normal temperature condition, and thereby two metal sample strips different from each other in the manufacturing conditions were prepared.

The metal strips were subjected to electrolysis by the SPEED, using the steel-derived particle extractor illustrated in FIG. 2. As the electrolytic solution, a 3% by mass methyl salicylate+1% by mass salicylic acid+1% by mass TMAC+ 0.05% by mass SDS dispersant system, capable of stably decomposing sulfides, was used. After the electrolysis, each metal sample strips was lightly washed with methanol, and placed in a beaker containing fresh methanol. The electrolytic solution was filtrated through a filter, also the resultant filter was placed in the beaker, and the particles precipitated in the surficial portion of the metal sample were allowed to disperse into the methanol solution under ultrasonic irradiation for approximately 1 minute.

Eight milliliters of the resultant liquid was placed in the liquid vessel for fine dispersion illustrated in FIG. 3, added with 2 ml of a 0.05% by mass SDS solution for dispersion, and the content was allowed to disperse under ultrasonic irradiation for approximately 5 minutes.

Figure 4:
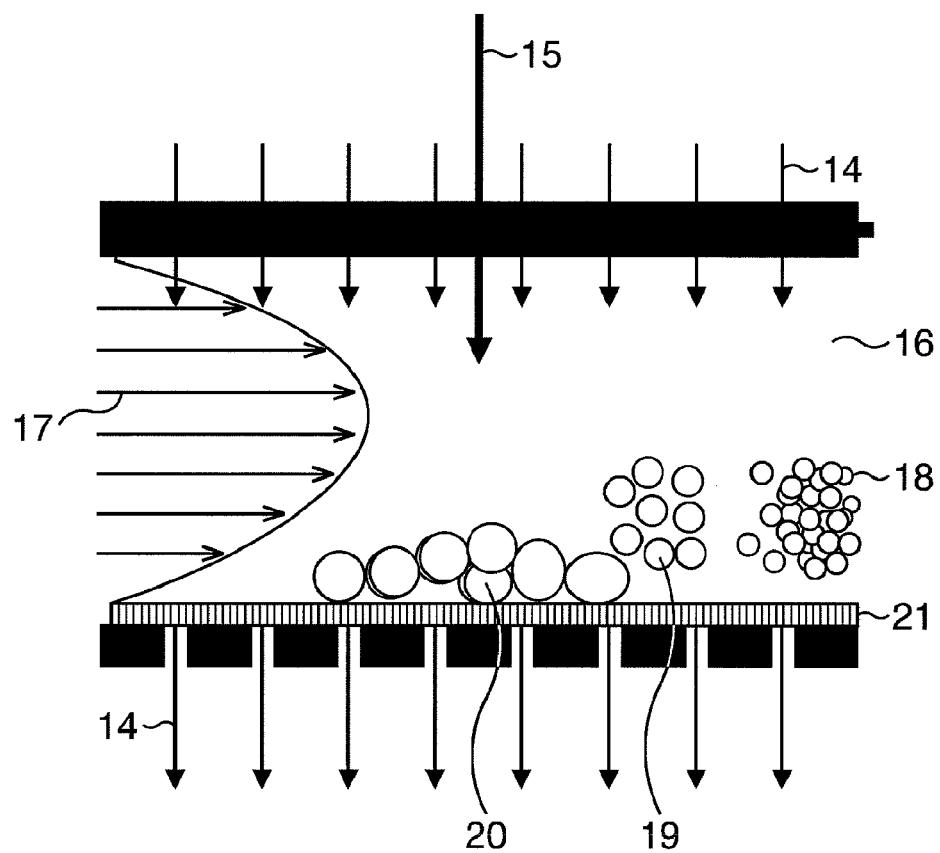
FIG. 4 is a drawing illustrating a principle of size fractionation based on the FFF process.
Figure 5:
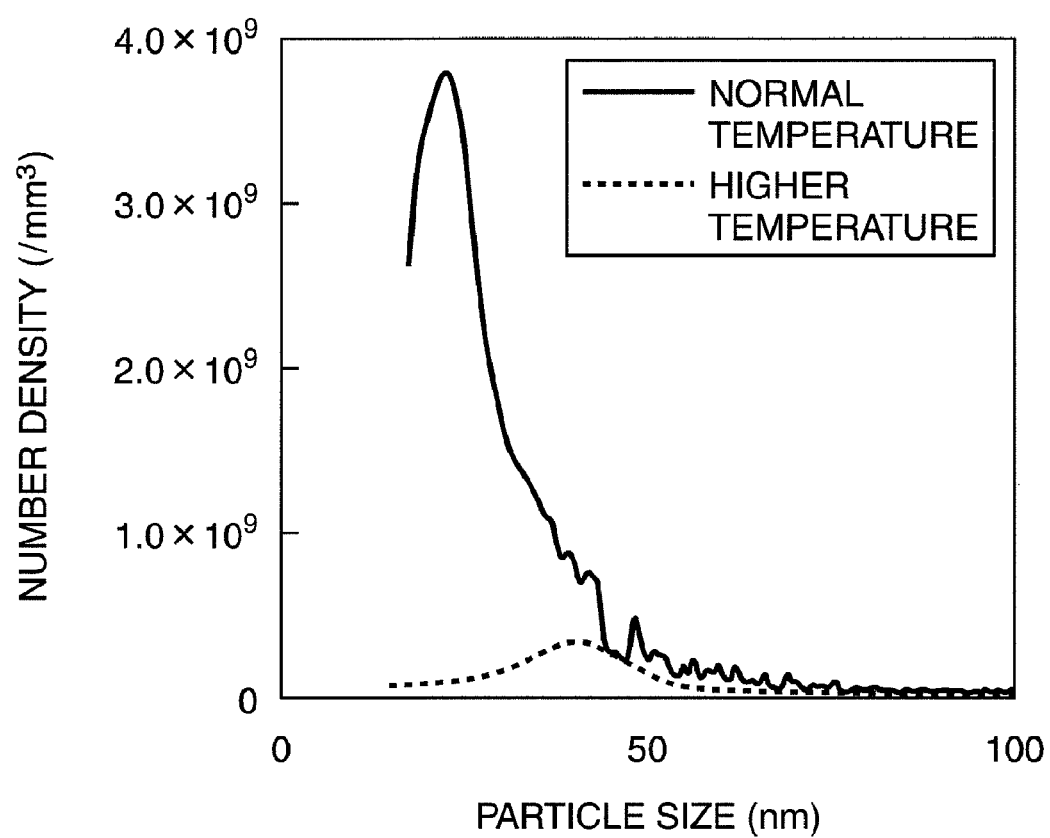
FIG. 5 is a graph illustrating results of measurement expressed by relation between particle size and number density distribution.

100 µl of the thus-dispersed liquid is placed in the FFF apparatus illustrated in FIG. 4, and measured by the FFF. Results are illustrated in FIG. 5. In FIG. 5, the abscissa represents the particle size, and the ordinate represents the number density. As can be illustrated in FIG. 5, when compared between two levels of temperatures of heating of the sample represented by the normal temperature and higher temperature, the sample heated under the normal temperature was found to have a large number of particles produced therein in the range of 50 nm or smaller, whereas the sample heated under the higher temperature was found to have coarse particles due to combination and growth of the 50 nm or smaller particles, because of the excessively high temperature.

From actual observation of the same liquid under a TEM, and preparation of a graph of particle size distribution, it was proved that the results of measurement illustrated in FIG. 5 were correct.

Figure 6:
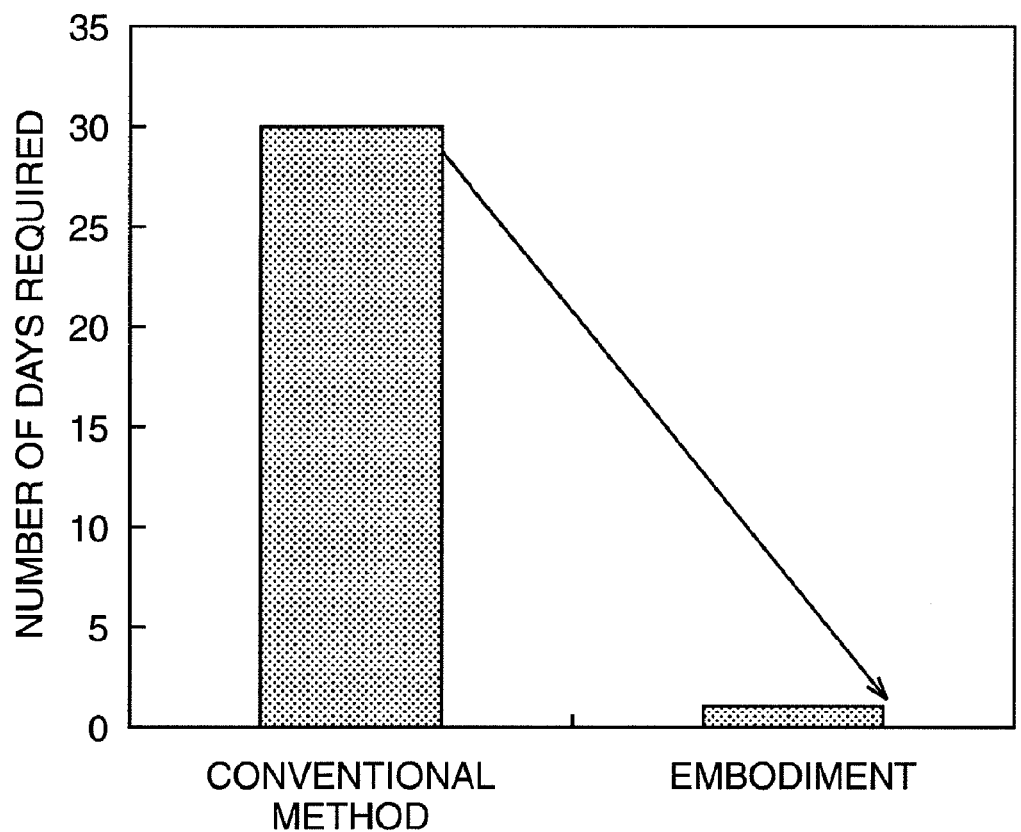
FIG. 6 is a graph illustrating results of comparison of the number of days required for analyzing number density between an embodiment of the present invention and a conventional method.

FIG. 6 illustrates results of comparison of the number of days required for analyzing the size, the number density, and a number density distribution function. The conventional method, by which the number density distribution is determined based on decision by photographs after microscopic observation, have needed approximately 30 days and advances skill of an operator in TEM observation and operation. In contrast, the required time according to the embodiment was approximately one day, including the process of dissolution.

Figure 7:
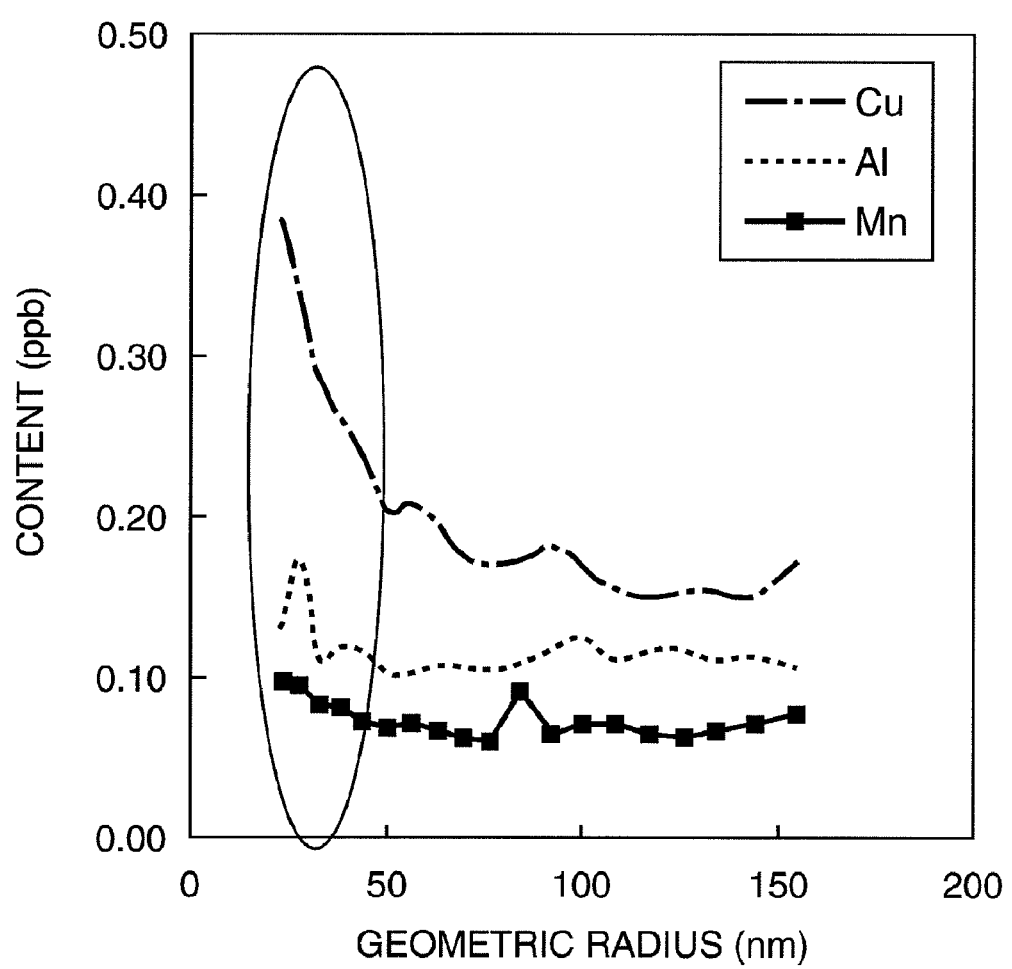
FIG. 7 is a graph illustrating results of compositional analysis of particles fractionated in the order of nanometers.

FIG. 7 is a graph illustrating results of compositional analysis of liquid discharged after being fractionated by size, and measured with respect to the size and the number density, using a general ICP (inductively coupled plasma) mass analyzer. The abscissa represents the particle size. As illustrated in FIG. 7, compositional changes in Al, Cu and Mn were clearly found to occur at approximately 10 nm pitches. Also information on the crystal structure of the particles extracted by size may be obtainable, if the solutions discharged herein by size are allowed to dry, and analyzed by a general X-ray crystal analyzer (XRD).

As has been described in the above, the number density distribution of the particles contained in the steel material may be obtained in an accurate and rapid manner. The density and size of the particles, suitable for manufacturing of high-quality steel and operation conditions at factories may rapidly be fed back. Even for the case where a mass production process of a new commodity is put into practical operation, or for the case where huge labor and cost may otherwise be needed by the general analytical method, materials may be evaluated in a rapid and inexpensive manner, by adopting the present invention. The present invention, therefore, ensures a large value of industrial use.

In addition, if analytical conditions were preliminarily determined, the operation may be standardized, and thereby the working efficiency may be improved to a large degree. While the conventional method was causative of individual difference specific to the sensory inspection, such as causing difference in the way of counting from person to person, the present invention is less likely to cause such individual difference, and thereby results of the particle distribution analysis may be obtained in a highly reproducible manner, if only analytical conditions may preliminarily be given. As a consequence, the technique of the present invention may be transferred to a large number of scenes where the particles in metal need be analyzed.

The preferred embodiments of the present invention have been explained referring to the attached drawings, of course without limiting the present invention. It is obvious that those skilled in the art may readily reach various changes and modified examples of the present invention without departing from the scope of the claims, and it is therefore understood that also these changes and modifications are in the technical scope of the present invention.

INDUSTRIAL APPLICABILITY

The present invention has a very large value in industrial use, typically as a technique of measurement suitable for tests for quality control of metal materials, and inspection procedures for rationalizing operational conditions at factories.

The invention claimed is:

1. A method of analyzing particle size distribution of particles in metal, comprising:
isolating, by extraction, particles contained in a metal material to be analyzed in a solution using a particle isolator;
dispersing the particles isolated by extraction into a solvent to prepare a dispersion, and fractionating the dispersion into a plurality of particle dispersions based on particle sizes, using a field flow fractionator; and irradiating laser light on each of the particle dispersions separated based on predetermined particle sizes, to thereby measure absolute values of the particle size based on angular dependence of reflection intensity, and also to thereby measure the number density based on magnitude of reflection intensity.

2. The method of analyzing particle size distribution of particles in metal according to claim 1, wherein the particles have sizes of 20 µm or smaller.

3. The method of analyzing particle size distribution of particles in metal according to claim 1, wherein the solvent is an organic solvent.

4. The method of analyzing particle size distribution of particles in metal according to claim 1, wherein a solvent containing a surfactant is used as the solvent.

5. The method of analyzing particle size distribution of particles in metal according to claim 1, wherein the particles are isolated by extraction based on an electrolytic method using a non-aqueous solvent system.

6. The method of analyzing particle size distribution of particles in metal according to claim 5, wherein the electrolytic method using a non-aqueous solvent system is a potentiostatic electrolytic method using a non-aqueous solvent system.

7. The method of analyzing particle size distribution of particles in metal according to claim 5, wherein isolation by extraction of the particles based on the electrolytic method using a non-aqueous solvent system is carried out with using a non-aqueous solvent base electrolytic solution containing a surfactant.

8. The method of analyzing particle size distribution of particles in metal according to claim 1, further comprising, after measuring the number density, analyzing composition of the particles.

9. The method of analyzing particle size distribution of particles in metal according to claim 1, further comprising, after measuring the number density, analyzing crystal structure of the particles.

* * * * *